(12) United States Patent
Dellimore et al.

(10) Patent No.: US 12,208,184 B2
(45) Date of Patent: Jan. 28, 2025

(54) BREAST PUMP DEVICE COMPRISING AN EXPRESSION KIT, A VACUUM UNIT AND A MILK EXPRESSION ASSESSMENT SYSTEM

(71) Applicant: KONINKLIJKE PHILIPS N.V., Eindhoven (NL)

(72) Inventors: Kiran Hamilton J. Dellimore, Utrecht (NL); Susanne Maaike Valster, Valkenswaard (NL); Anna Santagostino Barbone, Vermezzo (IT); Doortje Van De Wouw, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 891 days.

(21) Appl. No.: 16/966,036

(22) PCT Filed: Jan. 10, 2019

(86) PCT No.: PCT/EP2019/050477
§ 371 (c)(1),
(2) Date: Jul. 30, 2020

(87) PCT Pub. No.: WO2019/149486
PCT Pub. Date: Aug. 8, 2019

(65) Prior Publication Data
US 2020/0353138 A1 Nov. 12, 2020

(30) Foreign Application Priority Data
Feb. 2, 2018 (EP) .................................. 18154980

(51) Int. Cl.
*A61M 1/06* (2006.01)
*G01F 22/00* (2006.01)
(Continued)

(52) U.S. Cl.
CPC .............. *A61M 1/06* (2013.01); *A61M 1/064* (2014.02); *G01F 22/00* (2013.01); *G01F 23/802* (2022.01);
(Continued)

(58) Field of Classification Search
CPC ........ A61M 1/06; A61M 1/062; A61M 1/064; A61M 1/066; A61M 1/067; A61M 1/068;
(Continued)

(56) References Cited

U.S. PATENT DOCUMENTS

2005/0059928 A1* 3/2005 Larsson ................. A61M 1/06
                                                    600/382
2010/0217148 A1* 8/2010 Binder ................. A61B 5/4312
                                                    600/547
(Continued)

FOREIGN PATENT DOCUMENTS

CN    104990599    10/2015
WO    2014/058430   4/2014
(Continued)

OTHER PUBLICATIONS

International Search Report and Written Opinion Dated Apr. 17, 2019 For International Application No. PCT/EP2019/050477 Filed Janaury 10, 2019.
(Continued)

*Primary Examiner* — Shefali D Patel
*Assistant Examiner* — William R Frehe (57) ABSTRACT

A breast pump device (1) comprises an expression kit (2) and a vacuum unit (3) configured to realize a pressure cycle in the expression kit (2). For a purpose of determining one or more milk expression characteristics such as total volume of expressed milk, the device (1) is equipped with an acoustic milk expression assessment system (6) including an acoustic sensor (61) and a processor (62) configured to
(Continued)

process an acoustic signal received from the sensor (61) during operation of the device (1) when a receptacle (4) is used with the device (1) for receiving expressed the milk. By recording sound during a pumping session, it is possible to determine a value of a time duration of a free fall of droplets of expressed the milk from the expression kit (2) to the receptacle (4), which can be taken as a measure of a number of interesting milk expression characteristics.

20 Claims, 3 Drawing Sheets (51) Int. Cl.
 G01F 23/00 (2022.01)
 G01F 23/80 (2022.01)
(52) U.S. Cl.
 CPC ....... A61M 1/06935 (2021.05); A61M 1/0697 (2021.05); A61M 2205/3375 (2013.01); A61M 2205/3379 (2013.01); A61M 2205/3576 (2013.01); A61M 2205/50 (2013.01); A61M 2205/581 (2013.01)
(58) Field of Classification Search
 CPC ................ A61M 1/069; A61M 1/0693; A61M 1/06935; A61M 1/0697; A61M 1/007; A61M 2210/1007; A61B 2018/00333; A61J 13/00
 See application file for complete search history.

(56) References Cited

U.S. PATENT DOCUMENTS

| | | | |
|---|---|---|---|
| 2011/0160656 A1* | 6/2011 | Johnson | A61M 1/06 604/74 |
| 2014/0263611 A1 | 9/2014 | Bauer | |
| 2016/0220743 A1* | 8/2016 | Guthrie | G06F 3/0482 |
| 2016/0287767 A1 | 10/2016 | Simmons | |
| 2017/0021068 A1 | 1/2017 | Gaskin | |
| 2017/0172485 A1* | 6/2017 | Makower | A61M 1/06 |
| 2017/0220753 A1 | 8/2017 | Gutherie | |
| 2018/0338716 A1* | 11/2018 | Rajala | A61B 5/4288 |
| 2021/0093759 A1* | 4/2021 | Bourquin | A61M 1/066 |

FOREIGN PATENT DOCUMENTS

| | | |
|---|---|---|
| WO | 2015120321 | 8/2015 |
| WO | 2016/044368 | 3/2016 |
| WO | 2017108555 | 6/2017 |

OTHER PUBLICATIONS

Madoumier et al., "Modelling the properties of liquid foods for use of process flowsheeting simulators: Application to milk concentration", Journal of Food Engineering 164 (2015) 70-89.
https://www.engineeringtoolbox.com/surface-tension-d_962.html "Surface Tension, Liquids surface tension—water, mercury, oils and more", Engineering ToolBox, (2005).
Hill, et al: "Comparison of Milk Output Between Breasts in Pump-Dependent Mothers", J Hum Lact 23(4), 2007.
Engstrom, et al: "Comparison of Milk Output from the Right and Left Breasts During Simultaneous Pumping in Mothers of Very Low Birthweight Infants", Breastfeeding Medicine, vol. 2, No. 2, 2007.
Kathleen Aeurbach: "Sequential and simultaneous breast pumping: a comparison", Int. J. Nurs. Strud.,vol. 27. No. 3. pp. 157-265. 1990.
Prime, et al: "Simultaneous Breast Expression in Breastfeeding Women Is More Efficacious Than Sequential Breast Expression", Breastfeeding Medicin, vol. 7, No. 6, 2012.
Kent, et al: "Volume and Frequency of Breastfeedings and Fat Content of Breast Milk Throughout the Day", Pediatrics vol. 117, No. 3, Mar. 2006.

* cited by examiner

BREAST PUMP DEVICE COMPRISING AN EXPRESSION KIT, A VACUUM UNIT AND A MILK EXPRESSION ASSESSMENT SYSTEM

CROSS REFERENCE TO RELATED APPLICATIONS

This application is the U.S. National Phase application under 35 U.S.C. § 371 of International Application No. PCT/EP2019/050477 filed Jan. 20, 2019, published as WO 2019/149486 on Aug. 8, 2019, which claims the benefit of European Patent Application Number 18154980.9 filed Feb. 2, 2018. These applications are hereby incorporated by reference herein.

FIELD OF THE INVENTION

In one aspect, the invention relates to a breast pump device comprising (i) an expression kit including a breast-receiving funnel, a milk outlet and an air outlet, (ii) a vacuum unit configured to realize a pressure cycle in the expression kit, including an air inlet for connection to the air outlet of the expression kit and a pump mechanism for sucking air from the expression kit, through the air outlet of the expression kit and the air inlet of the vacuum unit, and (iii) a milk expression assessment system.

In another aspect, the invention relates to an assembly of a breast pump device and an external device or system which is configured to provide information to a user.

In yet another aspect, the invention relates to a method for determining milk expression characteristics during a milk pumping session performed by means of a breast pump device comprising an expression kit including a breast-receiving funnel, a milk outlet and an air outlet, and a vacuum unit configured to realize a pressure cycle in the expression kit, including an air inlet for connection to the air outlet of the expression kit and a pump mechanism for sucking air from the expression kit, through the air outlet of the expression kit and the air inlet of the vacuum unit.

BACKGROUND OF THE INVENTION

In general, a breast pump device is a well-known tool for extracting milk from a breast of a lactating woman, or two breasts simultaneously. Breast pump devices may be used in various situations, for example, if a baby or infant is not capable of extracting milk from the breast, or if a mother is separated from her baby or infant and the baby or infant is to be fed with breast milk at a later stage, by the mother or another person. Hence, breast pump devices are used by women to express breast milk at a convenient time, to be stored for later consumption by their/a baby or infant. Breast pump devices may also be helpful in a situation in which it is desired to stimulate and increase milk production in women with a low milk supply or to relieve pressure from engorged breasts.

A breast pump device is typically operated with one or two expression kits. Among other things, an expression kit comprises a breast-receiving funnel for receiving a woman's breast, which funnel may be equipped with pads or the like for massaging the breast in a certain way, and is designed for connection to a vacuum unit for realizing a pressure cycle in the expression kit, by means of which milk expression from the breast is enabled. In practical cases, the vacuum unit comprises an electric vacuum pump device, but manually operated breast pump devices are also known and used in practice. The fact is that by generating a pressure cycle, particularly a vacuum cycle, possibly accompanied by a certain way of massaging the breast, a simulation of a feeding action is obtained, which triggers the necessary let-down reflex in the lactating woman using the breast pump device. For the sake of completeness, it is noted that the term "vacuum" as used in this text refers to a relatively low pressure, i.e. a pressure that is significantly lower than ambient pressure.

Breast milk which is obtained as a result of a pumping session performed by means of a breast pump device is often intended for use at a considerably later stage than the time that the pumping session took place. The milk is normally stored in a fridge or freezer, in which case the milk is heated prior to feeding it to a baby or infant. In view of the fact that each baby or infant needs a specific volume of milk, it is important to keep track of the total volume of milk in stock. In particular, it may be determined whether the total volume of milk is sufficient for one or more upcoming feeding sessions of the baby or infant and/or how much milk should preferably be expressed in one or more upcoming pumping sessions.

For the purpose of being able to decide whether there is enough milk volume for a baby or infant, it is possible for a mother or other caregiver of the baby or infant to get an impression of the total volume which is available by looking in the fridge or freezer where the milk is stored. Another option is that the mother or other caregiver keeps track of the stored milk volume in a journal, either on paper such as by means of a notebook or electronically such as by means of a spreadsheet, in which case there is no need for visual inspection. In both cases, it is required to manually add up the separate milk volumes in order to determine the total milk volume. In the latter case, it is also possible to keep track of the consumption of the milk. Another option is to use a smartphone application or computer program which is designed to keep track of the total milk volume besides possible other useful functionalities. Still, in such a case, it is necessary for the mother or other caretaker to perform an action of providing the application or program with input about expressed milk volumes and milk consumption.

WO 2014/058430 A1 relates to a breast pump device which comprises a pump for generating suction and a controller configured to control the pump to generate different suction levels in a cyclic manner at a frequency, to control the pump to start and stop pumping, to collect input from a user of an amount of milk collected, and to store information for at least one pumping session. In an embodiment, the breast pump device comprises a graphical user interface on a touch screen display for the controller. The graphical user interface includes a pump control tab having one or more of a start/stop button, a session duration time clock, a suction control portion, and a speed control portion, a milk volume entry tab having one or more of a left breast milk volume entry portion, a right breast milk volume entry portion, a save button, and a session information portion; and a session history tab having one or more of scrolling control portions, and a session history information portion. The tabs provide a way for a user to switch between various modes of operation, e.g. pump control, milk volume entry, and viewing of session history. The touch screen display may display at least one of session duration time, current pump suction level, current cycle speed level, current volume status (e.g. on or mute), and current battery status. In addition, the touch screen display may provide session history information which has been saved by the user in respect of one or more pumping sessions, including one or more of date, time, left milk volume level, right milk volume level, suction level, speed, and duration.

US2016/287767 discloses a breast pump with an improved feedback milk extraction system. The system may communicate with various electronic devices and/or server components to exchange data and perform certain functionalities. The functionalities may include providing visual and audio feedback to a user, supporting unique kit identification as well as associated user profiles and preferred configuration settings, detecting and responding to leaks having various sizes during operation of the breast pump, controlling operation of the breast pump in response to detected leaks and the detected type and/or magnitude of the leak, preemptively contacting customers if a fault condition is detected or imminent, enabling effective labeling of collection containers, and determining volume and flow of expressed breastmilk.

SUMMARY OF THE INVENTION

In view of the foregoing, it is an object of the invention to provide a breast pump device of a new design, particularly a new design which allows for automatically determining, during a milk pumping session, a total volume of expressed breast milk, so that a mother or other caregiver can be unburdened, at least as far as the need to have information about pumped milk volumes is concerned. More in general, it is an object of the invention to provide a breast pump device, which is adapted to automatically determine one or more milk expression characteristics of a pumping session in a reliable manner.

To this end, the invention provides a breast pump device, comprising (i) an expression kit including a breast-receiving funnel, a milk outlet and an air outlet, (ii) a vacuum unit configured to realize a pressure cycle in the expression kit, including an air inlet for connection to the air outlet of the expression kit and a pump mechanism for sucking air from the expression kit, through the air outlet of the expression kit and the air inlet of the vacuum unit, and (iii) an acoustic milk expression assessment system including an acoustic sensor and a processor configured to process an acoustic signal received from the acoustic sensor during operation of the breast pump device when a receptacle is used with the breast pump device for receiving milk from the milk outlet of the expression kit.

The invention relies on applying acoustic techniques for automatically determining an expressed milk volume during pumping, and/or for automatically determining one or more other milk expression characteristics if so desired. In order to have optimal ease of use, the invention may involve communication of an automatically determined milk volume to a smartphone application or computer program, for example, which application or program may furthermore be designed to track other features of a pumping session, such as starting time, duration and expression rate.

During a pumping session, under the influence of the pressure cycle, a repetitive process takes place in which freshly expressed breast milk is allowed to accumulate in the expression kit, at a position upstream of the milk outlet, and is allowed to fall from that position, through the milk outlet. A first basic insight underlying the invention is that the moment that a quantity of milk is released, which will hereinafter be referred to as the release moment, can be known and/or determined, and that it is also possible to determine the moment that a quantity of milk hits a surface after having been released, which will hereafter be referred to as end-of-flight moment, as this latter moment involves a generation of sound and has a specific acoustic signature. A second basic insight underlying the invention is that a value of a time duration between the release moment and the end-of-flight moment, which will hereinafter be referred to as free fall time duration, can be taken as a measure of a total milk volume as present in a receptacle for receiving the milk. The fact is that the more milk that is present in a receptacle, the lower is the value of the free fall time duration. The surface mentioned in respect of the end-of-flight moment can be a surface of the receptacle or a surface of a volume of milk as present in the receptacle. The larger the total volume of milk, the higher the level of the milk in the receptacle, and the earlier the generation of sound of a quantity of milk hitting a surface after having been released.

Within the framework of the invention, any suitable type of receptacle may be used. As is the case in many conventional situations, the expression kit may be provided with screw thread at a position around the milk outlet, so that it is possible to screw a receptacle to the expression kit at an appropriate position for receiving milk from the expression kit during operation of the breast pump device. Nevertheless, other possibilities of attaching a receptacle to the breast pump device are also covered by the invention.

Determining milk expression characteristics on the basis of a detection of sound appears to be an advantageous concept which offers various interesting possibilities, as will now be explained.

In a practical embodiment of the breast pump device according to the invention, the processor is configured to process an acoustic signal received from the acoustic sensor during operation of the breast pump device according to a routine in which a value of a time duration between a release moment and a first moment following the release moment that a spike (peak) in the acoustic signal appears is determined, a release moment being a moment at which a release of vacuum takes place during the pressure cycle and at which an associated release of milk through the milk outlet takes place. As already explained in a general sense in the foregoing, a pumping session involves a repetitive process of accumulation of freshly expressed milk in the expression kit and release of the milk through the milk outlet. When vacuum is applied in the pressure cycle, milk is retrieved from a woman's breast. When vacuum is released in the pressure cycle, the milk is allowed to exit the expression kit through the milk outlet, so that it happens at that time that milk falls down, into a receptacle which is used with the breast pump device for receiving milk from the milk outlet, until the milk hits a surface of the receptacle, or, in case that the surface of the receptacle is covered by a volume of milk, a surface of the milk as present in the receptacle, thereby causing a spike in the acoustic signal. Once the value of the time duration between the release moment and the first moment following the release moment that a spike in the acoustic signal appears, which is the end-of-flight moment, is determined, a value is obtained which is directly related to the total milk volume in the receptacle and which is therefore suitable to be used in a process of determining an actual value of the total milk volume in the receptacle.

When the invention is applied, the end-of-flight moment is derived from interpretation of an acoustic signal. However, the release moment can be determined in any suitable way. In this respect, it is noted that the routine may involve determining the release moment from at least one of a spike in the acoustic signal and an actual control signal of the pump mechanism.

The processor may particularly be configured to perform a milk volume calculation on the basis of the value of the free fall time duration and values related to dimensional characteristics of the receptacle, a milk volume calculation being a calculation of an actual volume of milk in the receptacle. As a first step, the milk volume calculation may involve a determination of a distance along which a quantity of milk which is released from a position in the expression kit and through the milk outlet freely falls down according to the following relation: $s=0.5*g*t^2$, in which s represents the distance, g represents the acceleration due to gravity and t represents the free fall time duration. As a second step, the milk volume calculation may involve a determination of a height of the milk in the receptacle according to the following relation: $h_m=h_c+h_v-s$, in which $h_m$ represents the height of the milk in the receptacle, $h_c$ represents the total height of the receptacle, and $h_v$ represents the height of the position from which the milk is released above the receptacle. On the basis of the fixed relation between a liquid level and a liquid volume in a given receptacle, an actual volume of expressed milk in a receptacle can be derived directly from a determination of the value of $h_m$.

Preferably, the acoustic milk expression assessment system is adapted to involve in the milk volume calculation a compensation of a tilted orientation of the expression kit and the receptacle attached thereto. The fact is that a tilted orientation of the expression kit and the receptacle attached thereto may be expected in many practical situations, particularly in view of the fact that a woman normally holds the expression kit and the receptacle attached thereto to her breast. In this respect, it is noted that the acoustic milk expression assessment system may include an inertial sensor located in the expression kit, in which case the processor may be configured to process an inertial signal received from the inertial sensor according to a routine in which a value of an acceleration in a z-direction is determined, a z-direction being a longitudinal direction of a body part of the expression kit where the milk outlet is located, and to involve in the milk volume calculation a determination of a correction value to the distance along which a quantity of milk which is released from a position in the expression kit and through the milk outlet freely falls down on the basis of an actual value of a tilting angle of the expression kit with respect to the vertical. Further, the processor may be configured to determine the correction value according to the following relations: $f=1/\cos(\theta)$, in which f represents the correction value and $\theta$ represents the tilting angle, and $\theta=\cos^{-1}[(|A_z/g|)]$, in which $A_z$ represents the acceleration in the z-direction.

It is advantageous if the processor is configured to assess whether the value of the free fall time duration is within a predetermined range of values and to only perform the milk volume calculation in respect of a value which is within the predetermined range, as this contributes to the accuracy of the acoustic milk expression assessment system. In particular, this enables functioning of the processor in which spikes in the acoustic signal which are not representative of a relevant moment can be ignored. Assuming certain dimensions of the expression kit and the receptacle, a range of realistically feasible values of the free fall time duration can be predetermined and programmed in the processor.

Especially in a case in which it is possible to use receptacles of different types with the breast pump device, it is advantageous for the breast pump device to comprise a user interface configured to receive input from a user about an actual type of receptacle and to transmit an associated information signal to the processor. Alternatively, the breast pump device may be equipped with some kind of system for automatically detecting the receptacle type. In both cases, it is practical if the receptacle is labeled in an appropriate manner. A system as mentioned may particularly be designed to enable the processor to have information about the total height of an actual receptacle and information about the relation between liquid level and liquid volume of an actual receptacle.

In a practical embodiment of the breast pump device according to the invention, the expression kit includes a valve assembly. In such a case, a position in the expression kit from which milk is released is a position of the valve assembly in the expression kit, and a release moment is a moment at which the valve assembly opens under the influence of a release of vacuum during the pressure cycle. The valve assembly may comprise a duckbill valve, for example.

Alternatively or additionally to being adapted to perform a milk volume calculation, the processor may be adapted to perform a calculation aimed at providing a user with a real-time indication of the fat content of expressed breast milk during a pumping session. It is a generally known fact that the foremilk is thinner and has a lower fat content than the hindmilk. Based on the insight that the fat content affects the surface tension, and that this may influence the acoustic signal of milk hitting a surface of the receptacle or a surface of a volume of milk as present in the receptacle, the invention provides a way of determining the fat content of the milk during a pumping session. For example, a user may be provided with a real-time indication whether the expressed milk can be qualified as foremilk or hindmilk, an indication of the fat content of the milk, an indication of the total (average) fat content of the milk, and/or a recommendation about how to make sure that a mixture of foremilk and hindmilk as envisaged is collected in a receptacle so as to have an optimal mixture for a feeding session without needing to take further (mixing) actions.

It is noted that the processor may be of any suitable type, and may be part of a Central Processing Unit (CPU) of the breast pump device which is furthermore configured to control operation of the breast pump device, particularly the pump mechanism.

In order to save energy, which is especially relevant when the breast pump device is a battery-driven device, it may be advantageous if the CPU is configured to activate the acoustic milk expression assessment system only after a predetermined time from the start of operation of the breast pump device. The insight underlying this option is that when it comes to determining the total volume of breast milk obtained as a result of a pumping session, it is only necessary to detect an acoustic signal and perform an analysis thereof during the last stages of the pumping session.

Preferably, the processor is configured to communicate with an external device or system which is configured to provide information to a user. Examples of such an external device or system are a smartphone, a smartwatch, a tablet, a laptop and a computer. The external device or system may be used to run an application/program for providing information about the breast pump device and pumping sessions performed by means of the device to a user. Communication to the external device or system is preferably wireless.

Various positions of the acoustic sensor are feasible within the framework of the invention. A practical and useful position may be a position at the expression kit, downstream of the breast-receiving funnel. In general, a position at which the acoustic signal to be detected is sufficiently strong and free from disturbing influences as much as possible is preferred. The acoustic sensor may comprise a microphone, for example, or a suitable pressure sensor or accelerometer.

The invention also relates to an assembly of a breast pump device and an external device or system comprising an acoustic sensor, which device or system is furthermore configured to provide information to a user, the assembly furthermore including a holder mechanism for holding the external device or system on the breast pump device or a receptacle for use with the breast pump device. In the context of the invention, it has been found that it may be practical not to equip the breast pump device with an acoustic sensor, but to provide an external device or system comprising an acoustic sensor and hold it on the breast pump device or the receptacle. For example, use may be made of the microphone which is normally present in a smartphone. By holding the smartphone on the breast pump device or the receptacle at an appropriate position, it is possible to detect the acoustic signal which is to be processed for the purpose of determining one or more milk expression characteristics. The holder mechanism may comprise a holder element which is an integral part of a breast pump device or the receptacle, but it may even be more practical if a holder element is provided which is connectable to and removable from the breast pump device or the receptacle.

In fact, the entire acoustic milk expression assessment system may be incorporated in an external device or system, in which case the external device or system is not only equipped with an acoustic sensor but also with a processor configured to process an acoustic signal received from the acoustic sensor. The various options as described in the foregoing in respect of the configuration of the processor are equally applicable in such a case.

The invention also relates to a method for determining milk expression characteristics during a milk pumping session performed by means of a breast pump device comprising an expression kit including a breast-receiving funnel, a milk outlet and an air outlet, and a vacuum unit configured to realize a pressure cycle in the expression kit, including an air inlet for connection to the air outlet of the expression kit and a pump mechanism for sucking air from the expression kit, through the air outlet of the expression kit and the air inlet of the vacuum unit, wherein a time duration between a moment that milk is released from the expression kit and a moment that a free fall of the milk ends and the milk hits a surface located at a lower level than the expression kit is determined by detecting sound.

A basic principle which may be applied when the method according to the invention is put to practice is that spikes in an acoustic signal are taken as indicators of the moment that a quantity of milk is released from the expression kit and the moment that a free fall of the quantity of milk ends and the quantity of milk hits a surface. In the foregoing, an explanation of the way in which the acoustic signal may be processed for yielding information about milk expression characteristics, especially an actual volume of milk in a receptacle, has already been provided.

In conformity with what has already been suggested in the foregoing, it is noted that it is possible to use an external device or system comprising an acoustic sensor, which device or system is furthermore configured to provide information to a user, with the breast pump device for the purpose of detecting the sound.

The above-described and other aspects of the invention will be apparent from and elucidated with reference to the following detailed description of a breast pump device according to the invention and various possible embodiments as well as various ways of controlling thereof.

BRIEF DESCRIPTION OF THE DRAWINGS

The invention will now be explained in greater detail with reference to the figures, in which equal or similar parts are indicated by the same reference signs, and in which.

DETAILED DESCRIPTION OF EMBODIMENTS

Figure 1:
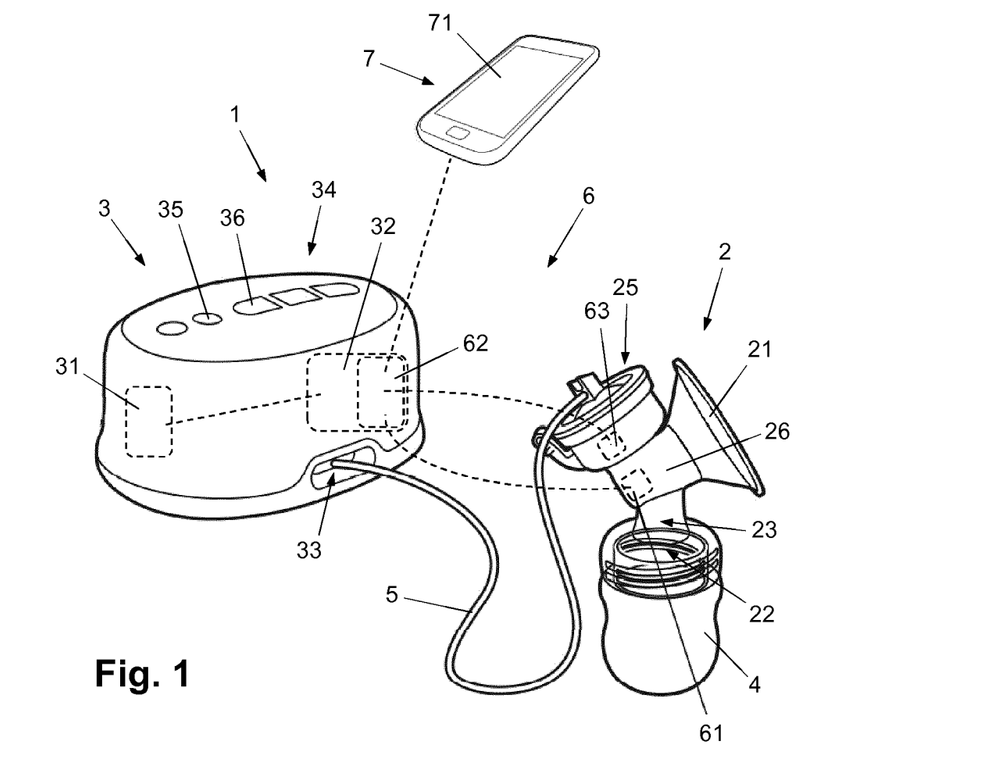
FIG. 1 diagrammatically shows a breast pump device comprising an expression kit, a vacuum unit, and a flexible hose interconnecting the expression kit and the vacuum unit, and also diagrammatically shows a smartphone for receiving information from the breast pump device and displaying information to a user.

The invention is in the field of breast pump devices and is especially applicable to electric breast pump devices. With reference to FIG. 1, a general description of an electric breast pump device will be given first so as to generate a clear picture of contextual aspects of the invention.

The breast pump device 1 comprises an expression kit 2 and a vacuum unit 3 for generating a pressure cycle during which vacuum (low pressure) is alternately generated and released. For the purpose of receiving expressed breast milk during operation of the breast pump device 1, a milk receptacle 4 is used which is connectable to the expression kit 2, e.g. by screwing, thereby closing a lower end of the expression kit 2. The vacuum unit 3 is an electric vacuum unit and comprises an electric pump 31 and an air valve for realizing an alternating vacuum during operation, i.e. during pumping sessions to be performed by means of the breast pump device 1. The pump 31, the air valve and a Central Processing Unit (CPU) 32 for realizing proper operation of the pump 31 and the air valve are designed to function in a manner which is well known in the field of breast pump devices. Therefore, further details of these components will not be explained in the present text, and the same is applicable to other practical aspects of the vacuum unit 3 known per se. The pump 31 is electrically connected to a source of electric power, which may be the mains or a battery, for example. The pump 31 and the CPU 32 are diagrammatically depicted in FIG. 1 as dashed rectangles, whilst the air valve is not shown. A path allowing for exchange of control signals etc. between the pump 31 and the CPU 32 is diagrammatically depicted in FIG. 1 as a dashed line. The path may be realized as any suitable type of communication wire, for example.

The expression kit 2 comprises a breast-receiving funnel 21, an aperture acting as a milk outlet 22, and a milk path 23 from the breast-receiving funnel 21 to the milk outlet 22. The breast-receiving funnel 21 is thus in fluid communication with the milk outlet 22 through the milk path 23. The milk path 23 is closeable by means of a valve assembly 24 (diagrammatically shown in FIG. 2), which comprises a duckbill valve in the shown example. The breast-receiving funnel 21 can comprise a massage cushion or the like (not shown) for providing a soft and warm feel to the breast and/or imitating a baby's or infant's sucking action.

In FIG. 1, the breast pump device 1 is shown in an assembled condition, in which the vacuum unit 3 is connected to the expression kit 2 through a flexible hose 5, wherein an air inlet 33 of the vacuum unit 3 is connected to an air outlet 25 of the expression kit 2. Such a configuration allows for a remote arrangement of the vacuum unit 3 with respect to the expression kit 2, so that the size of the part of the breast pump device 1 which is to be applied to a woman's breast can be kept within reasonable limits. It is to be noted that the breast pump device 1 can comprise two expression kits 2 for enabling a lactating woman using the breast pump device 1 to extract milk from two breasts at the same time, in which case the expression kits 2 can share a common vacuum unit 3.

Advantageously, as shown, the breast pump device 1 comprises a user interface 34 for allowing a user to control operation of the breast pump device 1. In the shown example, the user interface 34 is arranged on the vacuum unit 3 and enables a user to provide input to the CPU 32. The user interface 34 may be realized in any suitable manner such as through a number of buttons as shown, or through a touch screen, for example. By way of example, it is noted that the user interface 34 may comprise one button 35 for activating a stimulation mode and three buttons 36 for choosing one of three expression settings.

The invention provides a way of automatically determining one or more milk expression characteristics during a pumping session, such as a volume of expressed breast milk received by the receptacle 4. To that end, the breast pump device 1 is equipped with an acoustic milk expression assessment system 6 including an acoustic sensor 61 and a processor 62 configured to process an acoustic signal received from the acoustic sensor 61 during operation of the breast pump device 1. In the shown example, the acoustic sensor 61 is a microphone which is integrated in the expression kit 2 at a position along the milk path 23, upstream of the valve assembly 24. That does not alter the fact that another type of acoustic sensor 61 such as a suitable pressure sensor or accelerometer may be used in the breast pump device 1 according to the invention. In the case of the acoustic sensor 61 being a microphone, it is preferred if the microphone is of the unidirectional or cardioid type to minimize external noise and to optimally pick up the acoustic signature of the falling milk droplets. Further, other positions of the acoustic sensor 61 are feasible within the framework of the invention. When it comes to minimizing background noise, adding suitable acoustic shielding is available within the framework of the invention.

Both the acoustic sensor 61 and the processor 62 are diagrammatically depicted in FIG. 1 as dashed rectangles. A path allowing for transmittal of an acoustic signal from the acoustic sensor 61 to the processor 62 is diagrammatically depicted in FIG. 1 as a dashed line. The path is preferably realized in a wireless manner, which should not be understood such as to imply that a wired path is not covered by the invention as well.

The processor 62 may be part of the CPU 32, as indicated in FIG. 1. Besides the breast pump device 1, FIG. 1 shows a smartphone 7 which is used for providing information generated by the processor 62 during operation of the breast pump device 1 to a user. The processor 62 is configured for communicating with the smartphone 7, wherein the smartphone 7 may be used to run an application designed to display relevant information about the breast pump device 1 and pumping sessions performed by means of the breast pump device 1 on the screen 71 of the smartphone 7, and possibly also to receive relevant input from a user, in which case the smartphone 7 serves as a user interface. A path allowing for exchange of information between the processor 62 and the smartphone 7 is diagrammatically depicted in FIG. 1 as a dashed line. The path is preferably realized in a wireless manner, which should not be understood such as to imply that a wired path is not covered by the invention as well.

In the following, the way in which the acoustic milk expression assessment system 6 works will be explained, wherein also details of a theoretical background of the functioning principle of the acoustic milk expression assessment system 6 will be given.

Figure 2:
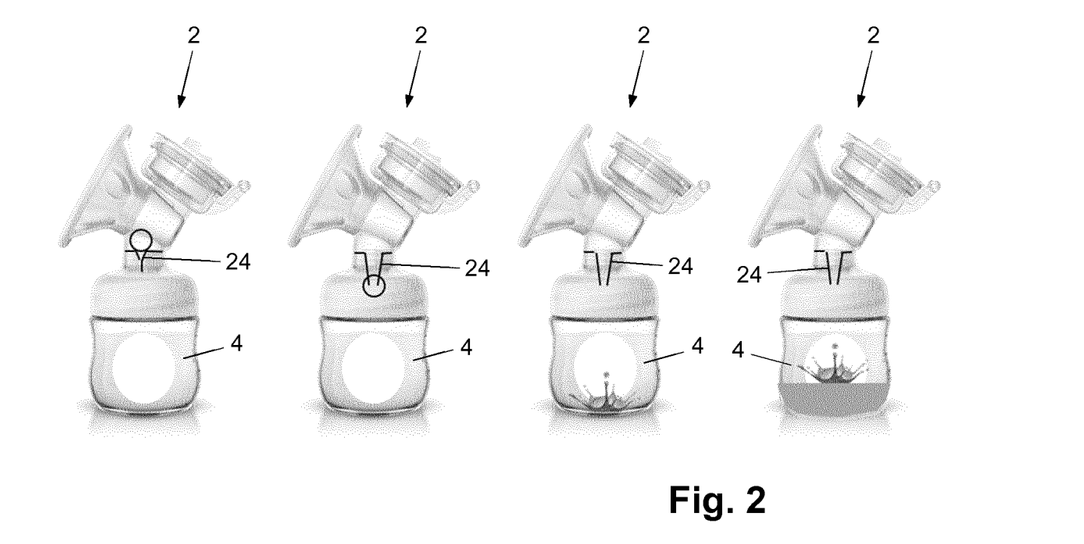
FIG. 2 illustrates various stages of expressed milk being collected in the expression kit, the milk being released towards a receptacle attached to the expression kit, and the milk hitting a bottom surface of an empty receptacle and a surface of a volume of milk in a receptacle which is partially filled, respectively.

In general, the breast pump device 1 is used to realize milk expression from a woman's breast. To that end, an alternating vacuum (pressure cycle) is applied to the breast. During periods of low pressure, or vacuum, the actual process in which milk is expressed from the breast takes place. Every time that the vacuum is released, freshly expressed milk drops in the receptacle 4. The quantity of milk which falls from the expression kit 2 is small and may be expected to appear from the expression kit 2 as a droplet. In FIG. 2, the first (most left) representation of an expression kit 2 and a receptacle 4 attached thereto serves to illustrate the fact that during a vacuum period, the valve assembly 24 is closed so that milk is collected above the valve assembly 24. Milk (to be) released from the expression kit 2 is diagrammatically depicted in FIG. 2 as a circle, and the valve assembly 24 is also diagrammatically depicted, by means of a number of lines. In the second representation of an expression kit 2 and a receptacle 4 attached thereto, it is illustrated that when the pressure is released, the milk falls into the receptacle 4. The third representation of an expression kit 2 and a receptacle 4 attached thereto serves to illustrate a situation in which the receptacle 4 is more or less empty and the milk which is released from the expression kit 2 ends up on a bottom surface of the receptacle 4, whereas the fourth representation of an expression kit 2 and a receptacle 4 attached thereto serves to illustrate a situation in which the receptacle 4 contains a volume of milk and the milk which is released from the expression kit 2 ends up on a surface of the volume of milk. It follows from a comparison of the third and fourth representation of an expression kit 2 and a receptacle 4 attached thereto that depending on the extent to which milk is present in the receptacle 4, the distance to be traveled by milk which is released from the expression kit 2 is longer or shorter. The time it takes for milk which is released from the expression kit 2 to hit a surface after having been released varies with the filling degree of the receptacle 4 as well, in a direct relation. Thus, by determining a value of a time duration between a release moment and an end-of-flight moment of milk falling from the expression kit 2 during the period of the pressure cycle that the vacuum is released, it is possible to obtain a realistic estimation of the level of milk in the receptacle 4 and thereby a realistic estimation of the volume of the milk which is present in the receptacle 4. Both moments can be derived from an acoustic signal detected by the acoustic sensor 61, as will now be explained with reference to FIG. 3.

Figure 3:
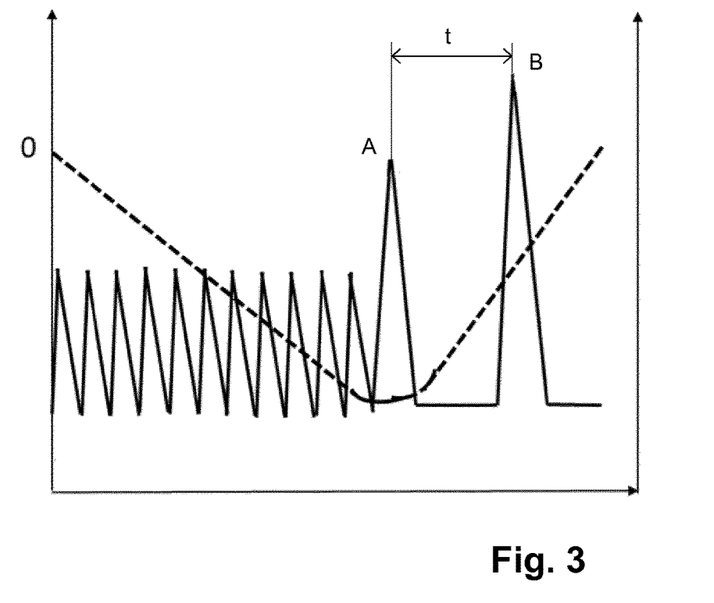
FIG. 3 is a theoretical graph illustrating a relation between pressure exerted by the vacuum unit, a level of sound recorded on the breast pump device or a receptacle attached to the expression kit, and time.

FIG. 3 is a graph of pressure exerted by the vacuum unit and sound level recorded by the acoustic sensor 61 against time. The left y axis of the graph is related to the pressure, the right y axis of the graph is related to the sound level, and the x axis of the graph is related to the time. The dashed line represents the pressure, and the continuous line represents the sound level. The left side of the graph is related to a situation in which the pump 31 is on, so that the pressure is below zero and gradually decreases to a minimum value. In this situation, the acoustic signal has a zigzag appearance, mainly as a result of the noise generated by the pump 31. At a certain moment, the pump 31 is switched off. As a result, the vacuum is gradually released, as can clearly be seen at the right side of the graph. The moment the pump 31 is switched off is characterized by a first spike A in the acoustic signal. For a short while, there is practically no sound, and then a second spike B in the acoustic signal appears, caused by the sound of milk hitting a surface in the receptacle 4. The value of the free fall time duration between the release moment and the end-of-flight moment is found by determining the time between the first spike A and the second spike B in the acoustic signal, knowing that the release moment occurs at the first spike A and the end-of-flight moment occurs at the second spike B.

At the core of the method for determining the volume of expressed milk in a receptacle 4 are the CPU 32 including the processor 62. At an input side of the CPU 32 and the processor 62, information about the release moments and the end-of-flight moments in a pumping session is obtained, wherein use is made of the acoustic sensor 61, at least for finding the end-of-flight moments. The release moments can be derived from the acoustic signal detected by the acoustic sensor 61 as well, but it is also possible that those moments are derived from a control signal of the pump 31. Another type of input to the CPU 32 and the processor 62 is input about dimensional characteristics of an actual receptacle 4. This input may be obtained in any suitable way, for example, from a user through a user interface, or from a detecting mechanism for automatically detecting the type of receptacle 4. The processor 62 is designed to calculate the value of the free fall time duration for a number of times milk is released from the expression kit 2. In particular, the processor 62 may be programmed to calculate an average value of the free fall time duration for a successive number of times that milk falls into the receptacle 4. The information about the free fall time duration can be used as a basis for estimating the volume of milk in the receptacle 4, as will now be explained.

The free fall of milk droplets from the expression kit 2 into the receptacle 4 during pumping is governed by the following kinematic equations for projectile motion: $v=u+a*t$ and $s=u*t+0.5*a*t^2$, in which v represents the final velocity of the milk droplets, u represents the initial velocity of the milk droplets, a represents the acceleration of the milk droplets, t represents the time duration of the free fall of the milk droplets, and s represents the distance of the free fall of the milk droplets. Knowing that the value of the initial velocity of the milk droplets is zero, as the milk droplets are released from a rest position, and that the acceleration of the milk droplets is the acceleration due to gravity, commonly represented by the symbol g, the following equations are obtained: $v=g*t$ and $s=0.5*g*t^2$. An average, commonly used value of the acceleration due to gravity is 9.81 m/s². As explained in the foregoing, the value of the free fall time duration is determined as the time difference between successive moments at which the milk droplets are released and moments at which the milk droplets hit a surface in the receptacle 4, i.e. between successive release moments and end-of-flight moments, wherein information about at least the latter moments is derived from an acoustic signal provided by the acoustic sensor 61.

For example, a 200 ml receptacle 4 having a total height of 7.7 cm is used, which can be filled to about a height of 6 cm, and a distance in the expression kit 2 between the position of the valve assembly 24 and the position for connecting to a top side of the receptacle 4 is 2.3 cm. In such a situation, the value of the distance of the free fall of the milk droplets varies between 7.7−6+2.3=4 cm and 7.7+2.3=10 cm, so that the value of the free fall time duration, which is represented by the equation $t=\sqrt{(2*s/g)}$, can be expected to vary between about 90 ms and 143 ms. It is advantageous to have information about the range of expected values, as this allows for ignoring spikes in the acoustic signal which are not related to the start and finish of the free fall of milk droplets, but are caused by disturbing noise instead. It is a notable fact that the equations presented in the foregoing are mass independent, i.e. do not depend on the mass of the milk droplets, since no external resultant force acts on the milk droplets during free fall in accordance with Newton's first law. Thus, it is very well possible for the processor 62 to apply a routine in which the value of the free fall time duration is the only variable to be obtained for the purpose of determining milk expression characteristics.

The volume of the milk in the receptacle 4 is directly related to the height of the milk in the receptacle 4. As a practical example, the following table of values is provided.

| Height from bottom of receptacle (cm) | Distance from valve assembly (cm) | Milk volume (ml) |
| --- | --- | --- |
| 0 | 10 | 0.0 |
| 1 | 9 | 20.0 |
| 2 | 8 | 46.5 |
| 3 | 7 | 76.5 |
| 4 | 6 | 103.5 |
| 5 | 5 | 145.0 |
| 6 | 4 | 176.0 |

Hence, once the value of the free fall time duration is calculated as the time difference between the release moment and the end-of-flight moment, the milk volume in the receptacle 4 can be determined through the distance information as can be derived from the free fall time duration. In the process, suitable audio data analysis programs and mathematic programs can be used. The processor 62 may be designed to provide more information than information about an actual milk volume in a receptacle 4. For example, by comparing milk volumes of different moments in time, a rate at which the receptacle is filled can be determined.

Figure 4:
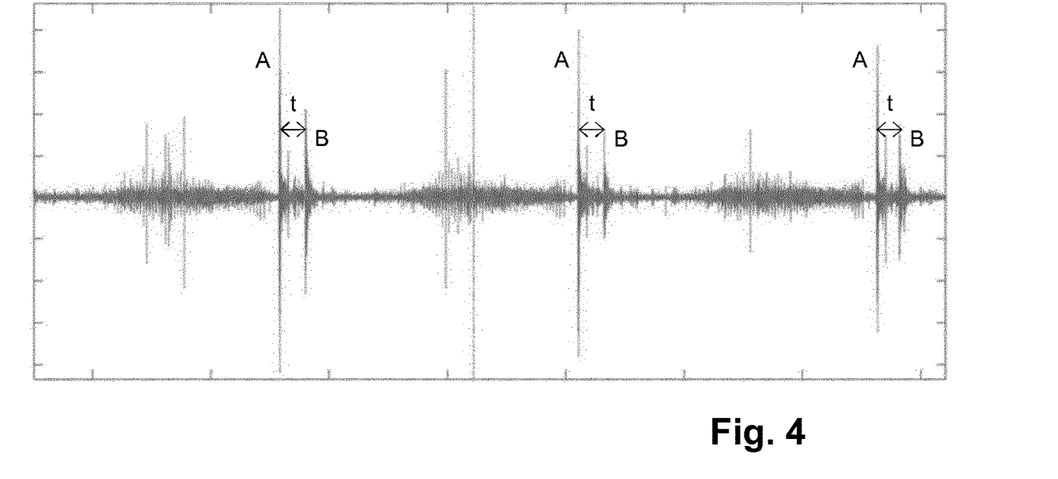
FIG. 4 is a graph illustrating a relation between a level of sound recorded on a breast pump device and time, obtained from an experiment which has been performed in the context of the invention.

FIG. 4 is a graph illustrating a relation between a level of sound recorded on a breast pump device 1 and time, obtained from an experiment which has been performed in the context of the invention. In the experiment, a microphone 61 was attached to the expression kit 2 of the breast pump device 1, at the side of a pump body portion 26 of the expression kit 2 which has an intermediate position between the breast-receiving funnel 21, the milk outlet 22 and the air outlet 25. The position of the microphone 61 was deliberately not chosen so as to be at the backside of the pump body portion 26, so as to avoid disturbance of the acoustic signal by freshly expressed milk spraying against that side. The acoustic signal was measured using the slow suction mode of the breast pump device 1, which mode is typically used after a milk let-down has occurred. Water was chosen so as to represent breast milk in the experiment, knowing that the properties of water are similar to the properties of milk. The receptacle 4 was filled with a water volume to a height of 5 cm. Water was supplied to the expression kit 2 through the breast-receiving funnel 21 by means of a milk bottle fitted with a thick-feed Y shaped teat. The sound pattern which was found in this way appears to correspond to the theoretical pattern as illustrated in the graph of FIG. 3.

It follows from the experiment that it is actually possible to identify similar patterns in each acoustic waveform with three main distinct and repeatable features.

A first phase of the acoustic signal represents a period during which the pump is on, and is characterized by a low amplitude signal following from operation of the motor unit of the pump 31 which decreases the pressure inside the pump body portion 26. During this phase of the acoustic signal, milk expression takes place, and milk is received from a woman's breast (as simulated in the experiment by extraction of water from the milk bottle with the Y shaped teat).

A second phase of the acoustic signal represents the event of the pump 31 being switched off and a milk droplet being released from the expression kit 2. When the pump motor is deactivated, the pressure in the pump body portion 26 of the expression kit 2 starts rising again to atmospheric. Under the influence of this release of vacuum, the valve assembly 24 moves from an initially closed position to an opened position. As a consequence, under the influence of gravity, expressed milk which has accumulated above the valve assembly 24 passes both the valve assembly 24 and the milk outlet 22, and falls in the receptacle 4 connected to the expression kit 2. This event is marked by a spike A in the acoustic signal caused by a suction membrane arranged in the air outlet 25 coming to a rest position.

A third phase of the acoustic signal represents the end of the free fall of a milk droplet from the expression kit 2. This event is marked by a spike B in the acoustic signal caused by the milk droplet hitting a surface in the receptacle 4 (represented by the surface of the water volume in the receptacle 4 in the experiment).

Experiments with the microphone 61 at other locations yielded useable acoustic signals as well, those signals being characterized by the same phases as described in the foregoing. The other locations which were tested include a position on the expression kit 2 at the level of the valve assembly 24, at which position the spikes A caused by the suction membrane arranged in the air outlet 25 coming to a rest position when the pump 31 is switched off are considerably smaller than the spikes A shown in FIG. 4, and at which position the low amplitude signal following from operation of the motor unit of the pump 31 is less apparent as well, and a position at the receptacle 4.

Figure 5:
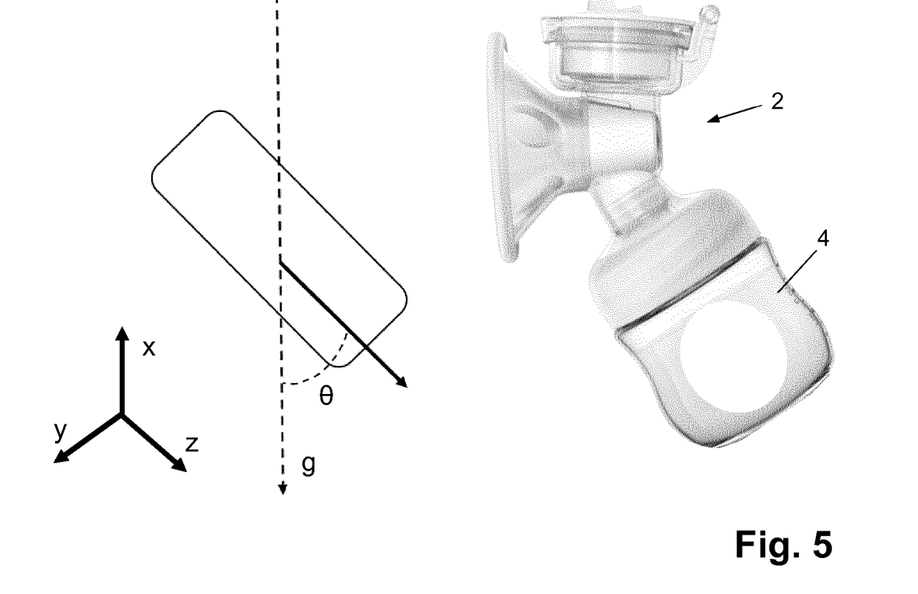
FIG. 5 illustrates various factors related to a tilted position of an expression kit and a receptacle attached to the expression kit.

A lactating woman can take several positions during a pumping session, varying from relaxed laid back to leaning forward. With reference to FIG. 5, it is noted that this affects the milk volume estimation based on the value of the free fall time duration, by influencing the time it takes for a milk droplet to reach a surface in the receptacle 4. Integrating an accelerometer, gyroscope or other inertial sensor 63 in the expression kit 2 or the receptacle 4 allows for the position and orientation of the expression kit 2 and the receptacle 4 connected thereto to be determined. Once determined, a correction factor can be applied to the estimate of the free fall time duration, so that the best possible accuracy of the milk volume estimation can be maintained. A correction value is computed based on the angle of the receptacle 4 with respect to the vertical (gravity vector), as follows: $f=1/\cos(\theta)$, wherein $\theta$ is determined by $\theta=\cos^{-1}[(|A_z|/g|)]$, in which f represents the correction value, $\theta$ represents the tilting angle, and $A_z$ represents the acceleration in a z-direction, i.e. a longitudinal direction of the pump body portion 26 of the expression kit 2. When the value of the detected free fall time duration is multiplied by the correction value, it is achieved that a possible tilted orientation of the receptacle 4 is compensated for.

At the right side of FIG. 5, a receptacle 4 in a tilted position is shown. At the left side of FIG. 5, the receptacle is diagrammatically depicted as a rectangle. In FIG. 5, directions labeled x, y and z are indicated by means of continuous arrows, whilst the vertical direction is indicated by means of a dashed arrow. The angle $\theta$ is indicated as being the angle between the vertical direction and the z-direction.

Two advantageous possibilities following from a repetitive determination of a value of a time duration of a free fall of milk droplets from the expression kit 2 are now mentioned and elucidated.

In the first place, it is possible to use the value of the free fall time duration for the purpose of automatically adjusting settings of a breast pump device 1. Via automatic detection of the pumped milk volume in a receptacle 4, the start of the milk let-down reflex can be noticed. The reason is that the pumped milk volume increases rapidly in a sudden manner at that time. When the start of the milk let-down reflex occurs, the settings of the pump 31 need to be adjusted, from quick shallow cycles to long deep cycles. Conventionally, this is done in a manual fashion by a user, but as a side effect of automatically keeping track of the volume of expressed milk, this can be done automatically as soon as a sudden increase of the volume is found.

In the second place, it is possible to use the value of the free fall time duration for the purpose of determining a speed at which milk expression takes place. Having information about the expression speed could help the lactating woman to optimize the pumping sessions. This information may be combined with further information from a pumping session, such as the total time duration of expression at a specific breast and applied suction strength setting of the breast pump device 1, and may be used for suggesting to the woman when is the best time to switch breasts in case milk is expressed from one breast only during the pumping session. Further, when the expression speed is known, it is possible to provide an estimation to the woman about how long it will most probably take to empty the breast, which may especially be relevant to a woman using the breast pump device 1 in a working environment.

In order to have the best possible accuracy of the determination of the milk volume, the processor 62 may be designed to employ at least one of the methods explained below.

The milk volume at a certain time of expression may be calculated by averaging the value of the free fall time duration over a predetermined time window of appropriate length, e.g. 10, 20 or 30 seconds. This will allow the range of expected and estimated values of the free fall time duration to be narrowed down.

It is possible to ignore spikes in the acoustic waveform signal detected after the spike A associated with the release of vacuum which yield a value of the time duration between spikes outside of an expected range of values (e.g. a range of 90 to 143 ms, as mentioned earlier). This ensures that only realistically feasible values of the time duration are used in the milk volume calculations.

By roughly knowing the time taken to express a certain volume of milk, or the expression rate, it is possible to ignore spikes associated with milk droplets of which the value of the time duration of their free fall at a specific time of expression is outside a given tolerance (e.g. ±10 or 20 ms).

In the event that double spikes occur, i.e. two consecutive spikes closely spaced in time, which both produce values of a time duration in the acceptable time window at a certain milk volume, it is possible to calculate the average between the two spikes and use this average in the milk volume calculation. This method is particularly useful when a double droplet is released from the expression kit 2.

In order to save energy, which may especially be desirable in the case of a battery-driven breast pump device 1, it is advantageous if the expressed milk volume is only estimated during the last stages of a pumping session. Based on total milk expression times of previous pumping sessions and the routine of the lactating woman at any given time of day or day of the week, an average total expression time could be calculated. This would then permit the acoustic sensor 61 to be only switched on for measuring values of the free fall time duration in the last 30-60 seconds of milk expression in order to determine the final, total milk volume expressed. For example, if a lactating woman typically expresses for 15 minutes per breast, the acoustic milk expression assessment system 6 may be turned on no earlier than at the start of the 15th minute.

During the first times a lactating woman uses the breast pump device 1, she could validate the detected value of the final milk volume by performing a visual assessment of the milk volume and providing the processor 62 with information about the actual milk volume through a user interface. This provides a basis for correcting discrepancies (systematic errors) between the automatically determined and actual values of the volume of expressed milk. A user interface may be provided in the form of a smartphone 7 running an application, as mentioned earlier.

Through a suitable user interface, the lactating woman could be offered the possibility of specifying a desired quantity of breast milk which she wants to obtain in a next pumping session. By automatically keeping track of the milk volume during a pumping session, the woman can be warned by means of a suitable signal and/or the breast pump device 1 can be automatically deactivated at the moment that the desired quantity appears to have been reached.

Figure 6:
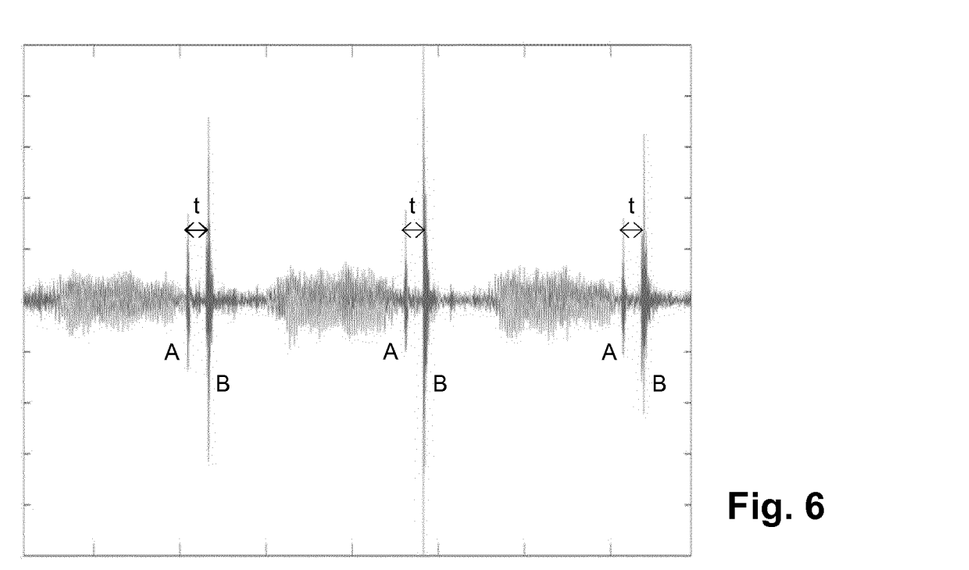
FIG. 6 is a graph illustrating a relation between a level of sound recorded on a breast pump device by means of a smartphone and time, obtained from another experiment which has been performed in the context of the invention.

FIG. 6 is a graph illustrating a relation between a level of sound recorded on a receptacle 4 by means of a smartphone 7 and time, obtained from another experiment which has been performed in the context of the invention. The experiment was performed in order to assess the feasibility of a possibility according to which the microphone on a smartphone 7 secured to a receptacle 4 is used to determine the expressed milk volume instead of modifying a breast pump device by adding an acoustic sensor 61. The smartphone 7 may be positioned on the receptacle 4 in such a way that the smartphone 7 extends beyond the receptacle 4 to some extent so that the microphone of the smartphone is more or less at the level of the valve assembly 24 of the expression kit 2 when the receptacle 4 is connected thereto. Also in this experiment, the receptacle 4 was connected to an expression kit 2, and water was supplied to the expression kit 2 through the breast-receiving funnel 21 by means of a milk bottle fitted with a thick-feed Y shaped teat. By means of the experiment, it was verified that the sound of liquid hitting a surface in a receptacle 4 can be recognized from a recorded acoustic signal, and particulars of the relevant spikes in the acoustic signal were found. It appears that the experiment yielded promising results, as can be seen in FIG. 6. In the acoustic signal which was obtained, the spikes A related to the moments that the pump 31 is switched off and the vacuum is released and the spikes B related to the moments that the free fall of milk droplets released from the expression kit 2 to the receptacle 4 ends are clearly distinguishable. Moreover, it appears that in this way, it is possible to detect an acoustic signal which is not so much influenced by sounds generated by the pump 31, so that it is easier to distinguish the milk droplets.

When it comes to holding a smartphone 7 or other external device or system to a receptacle 4, any suitable holder mechanism can be designed and applied. In general, such a suitable holder mechanism may comprise a holder which is designed to wrap around the receptacle 4 securely and which is also capable of securely holding the smartphone 7, wherein it is preferred if the holder can be adapted to use with receptacles 4 of various diameters, for example on the basis of flexible properties.

Using a smartphone 7 or similar device also offers the option of performing measurements aimed at compensating for a tilted orientation of a receptacle 4 in a process of determining the total milk volume in the receptacle 4. In that respect, there is no need to provide a separate unit such as an accelerometer or gyroscope, as the internal inertial sensor of the smartphone 7 may be used.

Additionally, any holder accessory could be devised for the support and positioning of any wireless earbuds/earphones near the desired sound detecting location on a breast pump device 1. The microphone of the earbuds/earphones could be used to collect information suitable for the purpose of estimating the total volume of expressed milk instead of the smartphone. This could be advantageously implemented using wireless earbuds/earphones which normally also include an accelerometer.

A process of detecting an acoustic signal for the purpose of determining a total volume of expressed milk and/or other milk expression characteristics can be very well performed in a context of a double electric breast pump device, i.e. a breast pump device which is designed to retrieve milk from two breasts simultaneously, and which comprises two expression kits 2. According to a first option, an acoustic sensor 61 could be integrated on each of the two expression kits 2, and the two acoustic signals obtained in that way could be analyzed for finding the information as required. According to a second option, it is possible to use only acoustic sensor 61 on only one of the two expression kits 2, provided that the acoustic sensor 61 is arranged at a position where it is possible to detect the sound of milk droplets falling in each of the receptacles 4 connected to the respective expression kits 2. The milk droplets falling in the one receptacle 4 can be distinguished from the milk droplets falling in the other receptacle 4 on the basis of the amplitude (or another suitable feature) of the detected spikes in the acoustic signal. In practice, this can be achieved by analyzing the amplitude of the spikes B related to the end-of-flight moments in the acoustic signals. The fact is that milk droplets falling in the receptacle 4 which is closest to the acoustic sensor 61 can be expected to generate sound at a larger amplitude than milk droplets falling in the receptacle 4 which is at a larger distance. In the context of a double electric breast pump device, it may be advantageous to use a bidirectional or an omnidirectional microphone as the acoustic sensor 61 rather than an unidirectional microphone.

It will be clear to a person skilled in the art that the scope of the invention is not limited to the examples discussed in the foregoing, but that several amendments and modifications thereof are possible without deviating from the scope of the invention as defined in the attached claims. It is intended that the invention be construed as including all such amendments and modifications insofar they come within the scope of the claims or the equivalents thereof. While the invention has been illustrated and described in detail in the figures and the description, such illustration and description are to be considered illustrative or exemplary only, and not restrictive. The invention is not limited to the disclosed embodiments. The drawings are schematic, wherein details which are not required for understanding the invention may have been omitted, and not necessarily to scale.

Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. Any reference signs in the claims should not be construed as limiting the scope of the invention.

Elements and aspects discussed for or in relation with a particular embodiment may be suitably combined with elements and aspects of other embodiments, unless explicitly stated otherwise. Thus, the mere fact that certain measures are recited in mutually different dependent claims does not indicate that a combination of these measures cannot be used to advantage.

The term "comprise" as used in this text will be understood by a person skilled in the art as covering the term "consist of". Hence, the term "comprise" may in respect of an embodiment mean "consist of", but may in another embodiment mean "contain/include at least the defined species and optionally one or more other species".

Notable aspects of the invention can be summarized as follows. A breast pump device 1 comprises an expression kit 2 including a breast-receiving funnel 21, a milk outlet 22 and an air outlet 25, and also comprises a vacuum unit 3 configured to realize a pressure cycle in the expression kit 2. For the purpose of determining one or more milk expression characteristics such as total volume of expressed milk, the breast pump device 1 is equipped with an acoustic milk expression assessment system 6, including an acoustic sensor 61 and a processor 62 configured to process an acoustic signal received from the acoustic sensor 61 during operation of the breast pump device 1 when a receptacle 4 is used with the breast pump device 1 for receiving milk from the milk outlet 22 of the expression kit 2. By recording sound during a pumping session, it is possible to determine a value of a time duration of a free fall of droplets of expressed milk from the expression kit 2 to the receptacle 4, which can be taken as a measure of a number of interesting milk expression characteristics.

The invention claimed is:
1. A breast pump device, comprising:
an expression kit including a breast-receiving funnel, a milk outlet, and an air outlet,
a vacuum unit configured to realize a pressure cycle in the expression kit, the vacuum unit including an air inlet for connection to the air outlet of the expression kit and a pump mechanism for sucking air from the expression kit through the air outlet of the expression kit and the air inlet of the vacuum unit, and
an acoustic milk expression assessment system including an acoustic sensor and a processor configured to process an acoustic signal received from the acoustic sensor during operation of the breast pump device when a receptacle is used with the breast pump device for receiving milk from the milk outlet of the expression kit,
wherein the processor is configured to process the acoustic signal received from the acoustic sensor during the operation of the breast pump device according to a routine which includes determining a value of a time duration in which a spike in the acoustic signal occurs between a release moment when a release of a vacuum takes place and a first moment following the release moment, the value of the time duration varying based on a distance along which a quantity of the milk freely falls down in an associated release from a position in the expression kit and through the milk outlet.

2. The breast pump device according to claim 1, wherein the routine involves determining the release moment from at least one of the spike in the acoustic signal and an actual control signal of the pump mechanism.

3. The breast pump device according to claim 1, wherein the processor is configured to perform a milk volume calculation based on the value of the time duration and values related to dimensional characteristics of the receptacle, the milk volume calculation being a calculation of an actual volume of the milk in the receptacle.

4. The breast pump device according to claim 3, wherein the distance along which the quantity of the milk freely falls down is from the position in the expression kit and through the milk outlet and is calculated according to the following relation: $s=0.5*g*t^2$, in which the s represents the distance, the g represents acceleration due to gravity and the t represents the time duration.

5. The breast pump device according to claim 4, wherein the processor is configured to involve in the milk volume calculation a determination of a height of the milk in the receptacle according to a following relation: $h_m=h_c+h_v-s$, in which the $h_m$ represents the height of the milk in the receptacle, the $h_c$ represents a total height of the receptacle, and the $h_v$ represents a height of the position from which the milk is released above the receptacle.

6. The breast pump device according to claim 4, wherein the acoustic milk expression assessment system includes an inertial sensor located in the expression kit, and wherein the processor is configured to process an inertial signal received from the inertial sensor according to a routine in which a value of an acceleration in the z-direction is determined, a z-direction being a longitudinal direction of a body part of the expression kit where the milk outlet is located, and to involve in the milk volume calculation a determination of a correction value to the distance along which the quantity of the milk which is released from the position in the expression kit and through the milk outlet freely falls down based on an actual value of a tilting angle (θ) of the expression kit with respect to a direction of vertical acceleration.

7. The breast pump device according to claim 6, wherein the processor is configured to determine the correction value according to following relations: $f=1/\cos(\theta)$, in which the f represents the correction value and the θ represents the tilting angle, and the $\theta=\cos^{-1}[(|A_z|/g)]$, in which the $A_z$ represents the acceleration in the z-direction.

8. The breast pump device according to claim 3, wherein the processor is configured to assess whether the value of the time duration is within a predetermined range of values and to only perform the milk volume calculation in respect of the value which is within the predetermined range.

9. The breast pump device according to claim 1, wherein the expression kit includes a valve assembly, and wherein the position in the expression kit from which the milk is released is a position of the valve assembly in the expression kit.

10. The breast pump device according to claim 1, wherein the processor is part of a central processing Unit (CPU) of the breast pump device which is furthermore configured to control the operation of the breast pump device.

11. The breast pump device according to claim 10, wherein the CPU is configured to activate the acoustic milk expression assessment system only after a predetermined time from a start of the operation of the breast pump device.

12. The breast pump device according to claim 1, wherein the processor is configured to communicate with an external device or system which is configured to provide information to a user.

13. A method of operating a breast pump device comprising an expression kit, a vacuum unit, and an acoustic milk expression assessment system, the method comprising:
realizing, by the vacuum unit, a pressure cycle in the expression kit, wherein the expression kit includes a breast-receiving funnel, a milk outlet, and an air outlet, and wherein the vacuum unit includes an air inlet for connection to the air outlet of the expression kit and a pump mechanism for sucking air from the expression kit, through the air outlet of the expression kit and the air inlet of the vacuum unit; and
processing, by a processor of the acoustic milk expression assessment system, an acoustic signal received from an acoustic sensor of the acoustic milk expression assessment system during the operation of the breast pump device when a receptacle is used with the breast pump device for receiving milk from the milk outlet of the expression kit and in accordance with a routine which includes determining a value of a time duration in which a spike in the acoustic signal occurs between a release moment when a release of a vacuum takes place and a first moment following the release moment, the value of the time duration varying based on a distance along which a quantity of the milk freely falls down in an associated release from a position in the expression kit and through the milk outlet.

14. The method according to claim 13, wherein the routine involves determining the release moment from at least one of the spike in the acoustic signal and an actual control signal of the pump mechanism.

15. The method of claim 13, further comprising:
performing, by the processor, a milk volume calculation based on the value of the time duration and values related to dimensional characteristics of the receptacle, the milk volume calculation being a calculation of an actual volume of the milk in the receptacle.

16. The method according to claim 15, wherein the distance along which the quantity of the milk freely falls down is from the position in the expression kit and through the milk outlet and is calculated according to a following relation: $s=0.5*g*t^2$, in which the s represents the distance, the g represents acceleration due to gravity and the t represents the time duration.

17. The method according to claim 16, wherein the processor is configured to involve in the milk volume calculation a determination of a height of the milk in the receptacle according to a following relation: the $h_m=h_c+h_v-s$, in which $h_m$ represents the height of the milk in the receptacle, the $h_c$ represents a total height of the receptacle, and the $h_v$ represents a height of a position from which the milk is released above the receptacle.

18. The method according to claim 16, wherein the acoustic milk expression assessment system includes an inertial sensor located in the expression kit, and wherein the processor is configured to process an inertial signal received from the inertial sensor according to a routine in which a value of an acceleration in a z-direction is determined, the z-direction being a longitudinal direction of a body part of the expression kit where the milk outlet is located, and to involve in the milk volume calculation a determination of a correction value to the distance along which the quantity of the milk which is released from the position in the expression kit and through the milk outlet freely falls down based on an actual value of a tilting angle (θ) of the expression kit with respect to a direction of vertical acceleration.

19. The method according to claim 18, wherein the processor is configured to determine the correction value according to following relations: $f=1/\cos(\theta)$, in which the f represents the correction value and the θ represents the tilting angle, and the $\theta=\cos^{-1}[(|A_z/g|)]$, in which the $A_z$ represents the acceleration in the z-direction.

20. The method according to claim 13, wherein the expression kit includes a valve assembly, and wherein the position in the expression kit from which the milk is released is a position of the valve assembly in the expression kit.

* * * * *